US00PP12052P2

(12) United States Plant Patent
Glicenstein

(10) Patent No.: US PP12,052 P2
(45) Date of Patent: Aug. 14, 2001

(54) AZALEA PLANT NAMED 'AMULET'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/590,628

(22) Filed: Jun. 8, 2000

(51) Int. Cl.[7] ..... A01H 5/00
(52) U.S. Cl. ..... Plt./238
(58) Field of Search ..... Plt./238, 239, 240

(56) References Cited

U.S. PATENT DOCUMENTS

P.P. 2,568 * 11/1965 Hahn ..... Plt./240

P.P. 10,508 * 7/1998 Stahnke et al. ..... Plt./238

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Azalea plant named 'Amulet', characterized by its very dark green glossy leaves that do not abscise during the cooling and forcing periods; large plant size; dense and outwardly spreading plant habit; vigorous growth habit; freely branching habit; uniform flowering response; numerous, very large, and showy dark purple-colored flowers; semi-double to double flower form; and excellent postproduction longevity with plants maintaining good flower substance for more than four weeks in an interior environment.

1 Drawing Sheet

BACKGROUND OF THE INVENTION

The present Invention relates to a new and distinct cultivar of Azalea, botanically known as *Rhododendron hybrida*, an evergreen greenhouse-forcing type of Azalea, and hereinafter referred to by the name 'Amulet'.

The new Azalea is a product of a planned breeding program conducted by the Inventor in Salinas, Calif. and Alva, Fla. The objective of the breeding program is to create new Azalea varieties having uniform plant habit, profuse and uniform flowering, dark green foliage, good foliage retention during the cooling and forcing periods, resistance to Cylindrocladium, and excellent postproduction longevity. The new Azalea originated from a cross made by the Inventor in March, 1992, in Salinas, Calif., of the cultivar 'Prize', disclosed in U.S. Plant Pat. No. 3,795, as the female, or seed, parent with the cultivar 'Alice Holland', not patented, as the male, or pollen, parent.

The new Azalea was discovered and selected by the Inventor as a flowering plant within the progeny of the stated cross in a controlled environment in Alva, Fla., in August, 1994. The selection of this plant was based on its semi-double to double flower form, dark purple flower color, very large flower size, uniform flowering response, improved foliage retention, and excellent postproduction longevity.

Asexual reproduction of the new Azalea by terminal cuttings taken in a controlled environment in Alva, Fla., has shown that the unique features of this new Azalea are stable and reproduced true to type in successive generations.

SUMMARY OF THE INVENTION

The new Azaela has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Amulet'. These characteristics in combination distinguish 'Amulet' as a new and distinct cultivar:

1. Very dark green glossy leaves that do not abscise during the cooling and forcing periods.
2. Large plants with dense and outwardly spreading plant habit; vigorous growth habit.
3. Freely branching habit.
4. Uniform flowering response.
5. Numerous, very large, and showy dark purple-colored flowers.
6. Semi-double to double flower form.
7. Excellent postproduction longevity with plants maintaining good flower substance for more than four weeks in an interior environment.
8. Very low incidence of infection with Cylindrocladium in inoculated trials.

Plants of the new Azalea differ from plants of the female parent, the cultivar 'Prize', in the following characteristics:

1. Plants of the new Azalea have much larger flowers than plants of the cultivar 'Prize'.
2. Plants of the new Azalea have semi-double to double flowers whereas plants of the cultivar 'Prize' have semi-double to double hose-in-hose flowers.
3. Plants of the new Azalea have dark purple-colored flowers whereas plants of the cultivar 'Prize' have dark rose pink-colored flowers.

Plants of the new Azalea differ from plants of the male parent, the cultivar 'Alice Holland', in the following characteristics:

1. Plants of the new Azalea retain their lower foliage better than plants of the cultivar 'Alice Holland'.
2. Plants of the new Azalea flower more uniformly than plants of the cultivar 'Alice Holland'.

3. Plants of the new Azalea have semi-double to double flowers whereas plants of the cultivar 'Alice Holland' have single flowers.
4. Plants of the new Azalea have dark purple-colored flowers whereas plants of the cultivar 'Alice Holland' have reddish purple-colored flowers.

Plants of the new Azalea can be compared to the plants of the cultivar 'Lavender Lace', disclosed in U.S. Plant Pat. No. 11,137. However, in side-by-side comparisons conducted by the Inventor in Salinas, Calif., plants of the new Azalea differed from plants of the cultivar 'Lavender Lace' in the following characteristics:

1. Foliage of plants of the new Azalea is less susceptible to amide injury than foliage of plants of the cultivar 'Lavender Lace'.
2. Plants of the new Azalea have semi-double to double flowers whereas plants of the cultivar 'Lavender Lace' have single flowers.
3. Plants of the new Azalea have dark purple-colored flowers whereas plants of the cultivar 'Lavender Lace' have lavender-colored flowers.
4. Plants of the new Azalea have longer postproduction longevity than plants of the cultivar 'Lavender Lace'.

BRIEF DESCRIPTION OF THE PHOTOGRAPHS

The accompanying colored photoraphs illustrate the overall appearance of the new Azalea. Thses photographs show the colors as true as it is reasonably possible to obtain in colored reproductions of this type. Colors in the photographs may differ slightly from the color values cited in the detailed botanical description, which accurately describe the actual colors of the new Azalea.

The photograph at the top of the sheet comprises a side perspective view of a typical plant of 'Amulet'.

The photograph at the bottom of the sheet is a close-up view of typical flowers of 'Amulet'.

DETAILED BOTANICAL DESCRIPTION

The aforementioned and following observations, measurements, values, and comparisons describe multiple plants grown in Salinas, Calif., in 12.5-cm containers in greenhouses during the spring under commercial production conditions. After sufficient flower bud development, plants were cooled at 3 to 5° C. for four weeks to break flower bud dormancy. Plants were subsequently forced into flower under commercial production conditions in a greenhouse. Plants described were about one year old.

In the following description, color references are made to The Royal Horticultural Society Colour Chart except where general terms of ordinary dictionary significance are used.

Botanical classification:

*Botanical.*—*Rhododendron hybrida* 'Amulet'.

*Commercial.*—Evergreen greenhouse-forcing type Azalea.

Parentage:

*Female or seed parent.*—*Rhododendron hybrida* cultivar 'Prize', disclosed in U.S. Plant Pat. No. 3,795.

*Male or pollen parent.*—*Rhododendron hybrida* cultivar 'Alice Holland', not patented.

Propagation:

*Type.*—By terminal vegetative cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Root description.*—Vigorous; finely-branched.

Plant description:

*Plant form and growth habit.*—Perennial, evergreen; outwardly spreading plant habit; inverted triangle; vigorous growth habit. Densely foliated. Freely flowering; numerous flowers per plant.

*Branching habit.*—Freely branching; about three lateral branches develop after removal of terminal apex.

*Plant height, soil level to top of flowers.*—About 31 cm.

*Plant diameter, area of spread.*—About 48 cm.

*Lateral branch description.*—Length: About 22.5 cm. Diameter at base: About 5.5 mm. Texture: Sparsely pubescent; fine brown hairs. Color: Immature: Close to 143D. Mature: Woody, between 164A and 165A.

Foliage description:

*Arrangement.*—Alternate, single.

*Length.*—About 4.6 cm.

*Width.*—About 2.5 cm.

*Shape.*—Elliptic.

*Apex.*—Cuspidate to mucronate.

*Base.*—Cuneate.

*Margin.*—Entire.

*Texture.*—Leathery, tough; durable; sparsely pubescent.

*Color.*—Young foliage, upper surface: Glossy; darker than 147A. Young foliage, lower surface: More green than 147B. Mature foliage, upper surface: Glossy; much darker than 147A. Mature foliage, lower surface: More green than 147B.

*Petiole.*—Length: About 9 mm. Diameter: About 3 mm. Color: Close to 147B.

Flower description:

*Natural flowering season.*—Spring after sufficient cool period. If forced, plants typically flower about 35 days after a four-week cooling treatment.

*Flower arrangement.*—Flowers arranged singly at terminals with usually about two or three flowers per apex. Flowers face upward and outward. Freely flowering. Not fragrant.

*Flower appearance.*—Very large semi-double to double flower form; stamens typically petaloid. Dark purple-colored petals. Flowers persistent.

*Flower diameter.*—About 9.4 cm.

*Flower depth.*—About 4.1 cm.

*Postproduction longevity.*—Under interior conditions, plants maintain good flower substance for more than four weeks.

*Flower bud* (*just starting to show petal color*).—Rate of opening: About three to four days depending on temperatures. Length: About 1.6 cm. Diameter: About 6 mm. Shape: Ovoid, elongated. Color: 61A.

*Petals.*—Arrangement: Semi-double to double flower form; single whorl of five fused petals surrounding stamens that are typically transformed into petaloids. Length: About 5 cm. Width: About 3.4 cm. Shape: Roughly spatulate with rounded apex. Margin: Entire; undulating. Texture: Smooth, velvety. Color: When opening, upper surface: Closest to 61A to 64A. When opening, lower surface: Closest to 61A to 64A. Fully opened, upper surface: More intense and between 64A and 64B; fading to 70A to 70B;

iridescent. Fully opened, lower surface: More intense and between 64A and 64B. Spots on upper petals: 53A to 59A.

*Petaloids.*—Quantity: Typically about six or seven. Appearance: Similar in color to petals, but smaller and irregular in size and shape. Length: About 3.2 cm. Width: About 2.1 cm. Shape: Irregular. Margin: Mostly entire; undulating. Texture: Smooth, velvety. Color: Fully opened, upper surface: More intense and between 64A and 64B; fading to 70A to 70B; iridescent. Fully opened, lower surface: More intense and between 64A and 64B. Spots on upper petaloids: 53A to 59A.

*Sepals.*—Arrangement: Single whorl of five sepals fused into a star-shaped calyx. Length: About 1.3 cm. Width: About 4 mm. Shape: Lanceolate with mostly acute apex. Margin: Entire. Texture: Very pubescent. Color, upper and lower surface: 144A, occasionally with anthocyanin, 59A, mostly distal.

*Peduncles.*—Length: About 1.7 cm. Diameter: About 2 mm. Angle: Upright. Strength: Flexible; strong. Texture: Very pubescent. Color: 144A to 144B.

*Reproductive organs.*—Androecium: Stamens: Typically transformed into petaloids. Gynoecium: Pistil quantity: One. Pistil length: About 3.7 cm. Stigma shape: Rounded. Stigma color: 59A to 59C. Style length: About 3.1 mm. Style color: Close to 59C. Ovary color: 144A; heavily whiskered.

*Seed.*—Seed production has not been observed.

Disease resistance: In inoculated trials that were conducted in Alva, Fla. during the summers of 1997 and 1999, a very low incidence of infection by Cylindrocladium was observed.

It is claimed:

1. A new and distinct Azalea plant named 'Amulet', as illustrated and described.

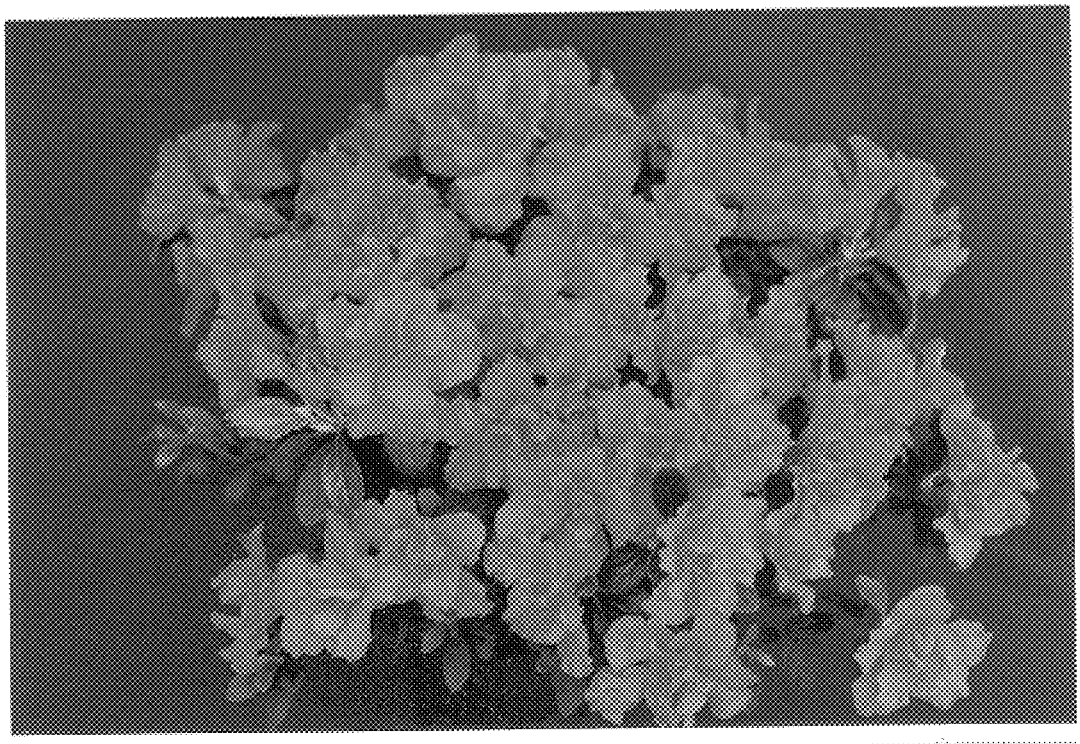
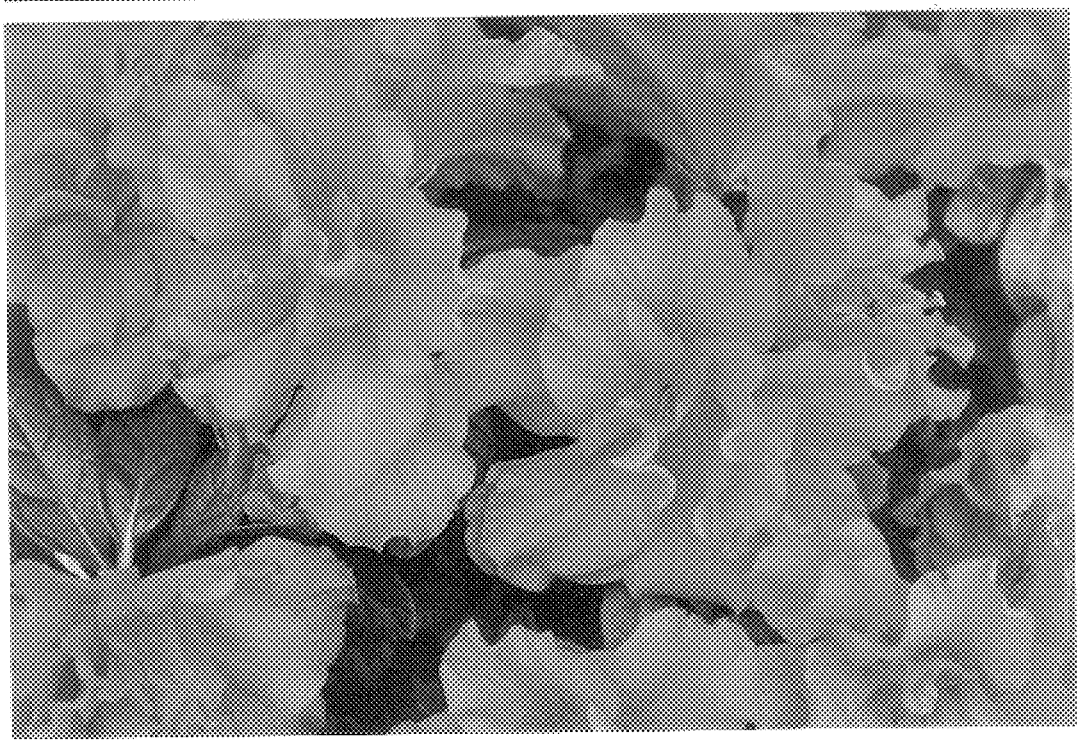

* * * * *